United States Patent [19]

Krüger et al.

[11] Patent Number: 5,648,566
[45] Date of Patent: Jul. 15, 1997

[54] METHYLENEPERFLUOROCYCLOALKANES AND THEIR USE IN THE PRODUCTION OF THERMOPLASTIC FLUORORESINS

[75] Inventors: Ralf Krüger, Köln; Michael Negele, Solingen; Norbert Lui, Köln; Albrecht Marhold, Leverkusen, all of Germany

[73] Assignee: Bayer Aktiengesellschaft, Leverkusen, Germany

[21] Appl. No.: 446,618

[22] PCT Filed: Dec. 9, 1993

[86] PCT No.: PCT/EP93/03470

§ 371 Date: May 31, 1995

§ 102(e) Date: May 31, 1995

[87] PCT Pub. No.: WO94/14738

PCT Pub. Date: Jul. 7, 1994

[30] Foreign Application Priority Data

Dec. 22, 1992 [DE] Germany ............ 42 43 526.9

[51] Int. Cl.$^6$ ............................................. C07C 17/02
[52] U.S. Cl. ................ 570/126; 570/124; 526/255; 526/254
[58] Field of Search .................. 570/124, 126; 526/255, 254

[56] References Cited

U.S. PATENT DOCUMENTS

| | | | |
|---|---|---|---|
| 2,879,309 | 3/1959 | Drysdale | 570/124 |
| 2,964,507 | 12/1960 | Knoth, Jr. | 526/255 |
| 3,046,261 | 7/1962 | Iserson et al. | |
| 3,274,265 | 9/1966 | Tatlow et al. | |
| 3,706,723 | 12/1972 | Chandrasekaran et al. | |
| 3,894,097 | 7/1975 | Vanderkooi, Jr. et al. | |
| 5,053,470 | 10/1991 | Wu | |

FOREIGN PATENT DOCUMENTS

| | | | |
|---|---|---|---|
| 649772 | 10/1962 | Canada | 570/124 |
| 1057427 | 2/1967 | United Kingdom | |
| 2143526 | 2/1985 | United Kingdom | |
| 9414738 | 7/1994 | WIPO | 570/124 |

OTHER PUBLICATIONS

FR 1557170, Gozzo et al; Feb. 14, 1969 Abstract.
I.L. Kumyats et al., Izvest. Alcad. Nauk. SSR, pp. 640–646 (1960).
J. March, "Advanced Organic Chemistry" 2nd ed., pp. 144–147, McGraw–Hill, New York (1977).
K. Rinehart et al., J. Am. Soc., vol. 83, pp. 225–231 (1961).
G. Camaggi et al., J. Chem. Soc. (C), pp. 925–936 (1971).

*Primary Examiner*—Joseph L. Schofer
*Assistant Examiner*—N. Sarofim
*Attorney, Agent, or Firm*—Sprung Horn Kramer & Woods

[57] ABSTRACT

Monomers of the formula (I) (for example, 3,3,4,4,5,5,6,6-octafluoromethylenecyclopentane) are described, as well as copolymers prepared from them and from one or more monomers copolymerizable with them.

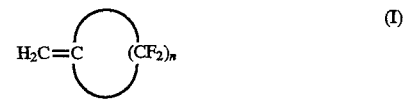

wherein n=3 to 5

The compounds are suitable for the production of a multiplicity of thermoplastically processable copolymers having various sets of properties which permit applications both as compact moulded parts and as coatings.

5 Claims, No Drawings

METHYLENEPERFLUOROCYCLOALKANES AND THEIR USE IN THE PRODUCTION OF THERMOPLASTIC FLUORORESINS

This application is based on the priority of International application Ser. No. PCT/US94/09661 filed Aug. 25, 1994.

It is known that hexafluoroacetone (U.S. Pat. No. 3,894, 097) or hexafluoroacetone hydrate (DE-A 3 425 907) react with diketene, acetic anhydride, acetic acid or acetone at temperatures of 340° C. to 1000° C. to form hexafluoroisobutylene (HFiB) via the intermediate compound bis (trifluoromethyl)-β-propiolactone (L. L. Kumyats et al., Izvest. Akad. Nauk. SSR, 640 (1960) (in English)).

It was not to be expected from prior art, and it is surprising, that the reaction of ketene-producing compounds such as diketene, acetic anhydride, acetic acid or acetone at temperatures of 340° C. to 1000° C. with perfluorocycloketones to form methyleneperfluorocycloalkanes in satisfactory yields is possible, in spite of the steric requirements of the spirolactone (J. March, Advanced Organic Chemistry, McGraw-Hill 1977, Chapter 4, pages 144 ff.) of the formula III which is formed as an intermediate compound.

Compared with the "HFiB process", according to the invention the methyleneperfluorocycloalkanes are obtained isomerically pure. The starting components and the by-products can be easily separated off (particularly from n=2) by virtue of the boiling points.

Fluoropolymers are always used in technology when particular properties are desired, such as low surface tension, high resistance to chemicals, oil and solvents, or extreme requirements as to the (heat) ageing stability combined with a high heat deflection temperature.

As the most widely-produced synthetic in the field of fluoropolymers, polytetrafluoroethylene (PTFE) combines the above-mentioned properties the most comprehensively. However, as is generally known, PTFE cannot be processed thermoplastically. Heat deflection temperature and gas permeability rapidly decrease at temperatures of above 100° C. An improvement in the thermoplastic processability is achieved through the introduction of comonomers, which reduce the viscosity of the polymer above the softening point (melting point in partly crystalline systems) and thereby improve the melt fusion. Examples of comonomers of this kind are hexafluoropropene and perfluorinated acyclic alkyl vinyl ethers. But in most cases the softening point of the copolymer is lowered by this measure, so that compromise solutions have to be accepted, depending on the intended application.

Other fluorine-containing homopolymers such as polyvinylidene fluoride or polychlorotrifluoroethylene can be processed thermoplastically but, owing to their lower fluorine content, they do not achieve the above-mentioned properties to the level which is achieved by the most highly fluorinated (co)polymers. Here also definite improvements can be obtained through copolymerisation.

According to a previously unpublished proposal by the Applicant, copolymers of perfluoro(cycloalkyl vinyl ethers) with VDF or CTFE show improved heat stabilities compared with the homopolymers.

Using the copolymers of VDF and hexafluoroisobutylene (HFiB) described in U.S. Pat. No. 3,706,723, higher melting temperatures (>=300° C.) are achieved than with pure PVDF (160° to 170° C.). Owing to the decomposition which is already beginning at 360° C., copolymers of this kind offer however only a narrow scope for processing (TOMMASI, G.: Fluoropolymers Conference 1992, Manchester). Moreover, highly toxic intermediate compounds appear during the synthesis of HFiB. Copolymers of HFiB with vinyl acetate (Vac) or vinyl alcohol (VOH) (U.S. Pat. No. 5,053, 470) are amorphous and show glass transitions at approximately 45° to 90° C. They are, however, unsuitable for many applications owing to their low glass transition temperatures, which are a measure of the thermoplastic softening.

The present invention provides new fluoromonomeric units of the formula (I)

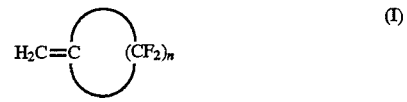

wherein n equals 3 to 5
wherefrom there can be produced a multiplicity of thermoplastically processable copolymers having different fluorine contents, which are distinguished by a high heat deflection temperature, heat stability and resistance to chemicals and, depending on the comonomer, possess differing adhesive properties and solubilities in organic solvents. Depending on the composition of the comonomer and the resulting set of properties, copolymers of this kind are suitable both for use in the field of thermoplastic moulded parts and for coatings.

Methylenefluoroalkanes having the formula (I) are new. The methylenefluoroalkane of the formula (I) having n equal to 4 has, to the knowledge of the Applicant, already been described only once as a hypothetical intermediate structure in an attempt to explain the end products formed in the irradiation of decafluorocyclohexane by UV light (see litterature reference).

For the first time methylenefluoroalkanes are in fact being made available, according to the invention, as stable end products having less than 30% by weight, preferably less than 10% by weight and particularly preferably less than 5% by weight, of contamination by foreign substances.

The methyleneperfluorocycloalkanes of the formula (I) were prepared from perfluorocycloketones of the formula (II) by conversion of the ketene-producing compounds diketene, acetic anhydride, acetic acid or acetone at temperatures of from 340° to 1000° C.

The ketene-producing compounds, for example diketene, can be used, for instance, in quantities of from 1 to 5 mol, referred to 1 mol of perfluorocycloketone of the formula (II).

Preferred reaction temperatures are in the range of from 400° to 700° C.

The compound of the formula (II) can only be reacted with the ketene-producing compound or mixed with inert gases, for example, nitrogen, in the gas phase.

The reaction can be carried out, for example, by feeding perfluorocycloketones of the formula (II) and ketene-producing compounds into one or more parallelly-arranged tubes made of an inert material and heating the tube or tubes to the desired reaction temperature. Quartz, for example, is suitable tubing material.

The tube or tubes can optionally be filled with lumps of inert materials, for example, with regularly or irregularly shaped pieces of quartz having an average diameter of from 1 mm up to one half of the internal diameter of the respective tube.

The gas mixture issuing from the reaction zone can be worked up, for example, by complete or partial condensation followed by isolation from the condensate, by means of distillation, of the methyleneperfluorocycloalkanes contained therein.

The spirolactones of the formula (III) which occur as by-products can likewise be converted into the desired methyleneperfluorocycloalkanes of the formula (I) by pyrolysis at temperatures of from 400° to 700° C., preferably 500° to 600° C.

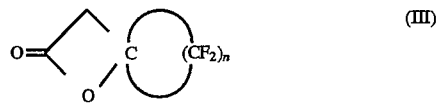

It has been found that methyleneperfluorocycloalkanes of the formula (I) copolymerise in good yields with certain fluorinated monomers such as vinylidene fluoride and vinyl fluoride, and with non-fluorinated monomers such as ethylene or vinyl esters of short-chain carboxylic acids such as, for example, vinyl acetate, vinyl propionate, vinyl butyrate or vinyl pivalate.

For instance, copolymers of methyleneperfluorocyclopentane and vinylidene fluoride give rise to high-melting polymers ($T_m$ up to 310° C.) having excellent temperature resistance and heat deflection temperature. Compared with perfluorinated thermoplastics, which are comparable with the copolymers according to the invention as regards their heat stability and resistance to chemicals, the copolymers according to the invention have higher heat deflection temperatures at lower fluorine contents.

By copolymerising the monomers according to the invention using vinyl esters such as, for example, vinyl acetate or vinyl propionate, amorphous copolymers are obtained which can be converted by hydrolysis partly or completely to the vinyl alcohol copolymers. Such copolymers from methylene-perfluorocycloalkanes and vinyl esters, as well as the corresponding partly or completely solvolysed products, have glass transition temperatures of above 100° C., are soluble in certain organic solvents and are therefore suitable as coating materials having good processing and bonding properties as well as the possibility of cross-linking on the one hand and the above-mentioned properties typical of fluoropolymers on the other.

The present invention also provides polymer compositions, which are obtainable through copolymerisation of a) from 10 to 52 mol-% of methyleneperfluorocycloalkane of the formula (I) and b) from 90 to 48 mol-% of monomers copolymerisable therewith, which can be either fluorine-containing, such as b1) vinylidene fluoride, vinyl fluoride, or can be fluorine-free, such as b2) ethylene, vinyl acetate or vinyl alcohol (by saponification of Vac-copolymers).

The preparation of the polymers according to the invention is carried out by a radical path. Apart from that, there is no limitation at all as regards the polymerisation method. Polymerisation can take place in solid form, in solution (suitable solvents are fluorocarbons, for example, hexafluorocyclopentane, perfluorobutane or chlorofluorocarbons, for example, trichlorofluoroethane), in suspension (with concomitant use of suspension stabilisers) or in emulsion (fluorinated emulsifiers are necessary).

The radical reaction can be started by high-energy radiation, thermally or by radical initiators. In principle compounds which are known and which are suitable for the respective reaction medium are employed for the chemical initiation.

Thus for solid polymerisation, solution polymerisation or suspension polymerisation, organic oil-soluble peroxides which can also be fluorinated are used, such as diisopropyl peroxydicarbonate, trifluoroacetyl peroxide or soluble organic azo compounds such as azobisisobutyronitrile. The initiators employed for the emulsion polymerisation are water-soluble inorganic per compounds, such as persulphates, perborates, percarbonates etc., generally in the form of their potassium, sodium or ammonium salts and, when lower temperatures are used, optionally in combination with decomposition accelerators, as a rule reducing agents. Reducing agents which can be used are sulphur compounds such as, for example, sodium sulphite, sodium pyrosulphite or Rongalit C (sodium formamidinesulphinate), also organic reducing agents such as ascorbic acid, metal salts such as iron (II) or cobalt (II) salts, organometallic compounds etc.

The polymerisation temperatures for the copolymerisation are between −30° and 90° C. preferably not higher than 70° C.

The copolymerisation using gaseous monomers is carried out under increased pressure. The said pressure should be at least 2 bar, but need not exceed 100 bar.

Linear copolymers having molecular weights of from $10^3$ to $10^6$ g/mol are obtained.

EXAMPLES

Example 1

3,3,4,4,5,5,6,6-octafluoromethylenecyclopentane and (1-hydroxyperfluorocyclopentyl)acetic acid-β-lactone 114 g of octafluorocyclopentanone (0.5 mol) and 70 g of freshly distilled diketene (0.833 mol) are introduced under a light stream of nitrogen at 500° C.(±10° C.) from two dropping funnels over a period of three hours into a glass reaction vessel, 30 cm in length (diameter approx. 18 mm) equipped with an electric heating coil. The volumes supplied are coordinated with one another so as to ensure that there is always a slight excess of ketene in the reaction vessel. The reaction gas is condensed at −78° C. and slowly brought to room temperature. Carbon dioxide and excess ketene are distilled off, during which approx. 5 g of entrained material can be collected in an ice-cooled trap connected in tandem. Subsequently the crude mixture (132 g) is coarsely distilled at normal pressure via a bridge.

(Bottom of column max. 110° C. temperature at top of column max. 80° C.); 68 g of distillate is obtained.

The coarse distillates are fractionated at normal pressure through a 40 cm packed column: in addition to the first runnings of octafluorocyclopentene (bp 26° to 28° C. 12 g) and an intermediate fraction (bp 30° to 62° C., according to GC 78% of the target product), 47 g of the target product (bp 64° to 67° C., according to GC 98.5%) is obtained. (1-hydroxy-perfluorocyclopentyl)acetic acid-β-lactone (16.5 g according to GC 85%) is recovered from the bottom of the coarse distillation and from the column distillation. Spectroscopic data from 3,3,4,4,5,5,6,6-octafluoromethylenecyclopentane:

$^1$H-NMR: δ=6.55 ppm (q, $J_{H-F}\approx$3 Hz,=CH$_2$) (optionally internal TMS in CDCl$_3$).

$^{19}$F-NMR: δ=−112.4 ppm (t, $J_{H-F}\approx$3 Hz, 2CF$_2$ beside=CH$_2$) and −135.4 ppm/t, 2CF$_2$) (optionally CFCl$_3$ in CDCl$_3$).

$^{13}$C-NMR: δ=111.2 ppm ($^1J^{C-F}\approx$266 Hz 4 CF$_2$); 129.5 ppm (s, β-C [CH$_2$=] and 134.6 ppm (q, α-C [$R_{f-C=}$], $^3J_{C-F}$=23 Hz) (optionally internal TMS in CDCl$_3$).

Spectroscopic data from (1-hydroxyperfluorocyclopentyl)-acetic acid-β-lactone:

$^1$H-NMR: δ=3.97 ppm (s, CH$_2$) (optionally internal TMS in CDCl$_3$).

$^{19}$F-NMR: δ=−136.8 ppm (quar, 2CF$_2$), −141.3 ppm (quar, 2CF$_2$) (optionally CFCl$_3$ in CDCl$_3$).

Example 2

40 g of (1-hydroxyperfluorocyclopentyl)acetic acid-β-lactone is introduced under a light stream of nitrogen at 550° C. over a period of 1 hour into a quartz reaction vessel 40 cm in length (diameter approx. 25 mm) filled with pieces of quartz. The reaction gas is condensed in a condenser and then distilled. The lactone undergoes 100% conversion. The yield of octafluoromethylenecyclopentane is 70%.

Example 3

In a manner similar to Example 1, 0.25 mol corresponding to 44.5 g of hexafluorocyclobutanone [in accordance with J. Amer. Chem. Soc. 83, 225 (1961)] and 35 g of diketene were reacted together.

66 g of condensate was isolated from which, after rectification at normal pressure, 22 g of 3,3,4,4,5,5-hexafluoromethylenecyclobutane having a boiling point of 42° to 44° C. was obtained (=49.5%).

Example 4

In a manner similar to Example 1, 0.5 mol corresponding to 139 g of decafluorocyclohexanone [in accordance with J. Org. Chem. 33, 2692 (1968)] and 70 g of diketene were reacted together.

195 g of condensate was isolated from which, after rectification at normal pressure, 86 g (=62.3%) of 3,3,4,4,5,5,6,6,7,7-hexafluoromethylenecyclobutane having a boiling point of 108° to 110° C. was obtained.

Example 5

Copolymerisation of vinylidene fluoride with methyleneperfluorocyclopentane 100 g of 1,1,2,2,3,3-hexafluorocyclopentane, 60 mg of diisopropyl peroxydicarbonate and 30 g of methyleneperfluorocyclopentane were placed, with stirring, in a 0.3 l autoclave and cooled to −6° C. The closed autoclave was then subjected three times to a nitrogen pressure of 10 bar and each time subsequently released to normal pressure. Subsequently 20 g of vinylidene fluoride was condensed into the autoclave. The reaction mixture was heated to 40° C. with constant stirring. After a total reaction time of 40 h at 40° C., the mixture was cooled. 15 g of a white pulverulent powder was isolated from the mixture by complete precipitation using ethanol and drying at 60° C. in a vacuum.

The copolymer is insoluble in trichlorotrifluoroethane (R113), acetone, dimethylformamide and dimethylacetamide.

The composition of the copolymer, determined by analysis of elemental fluorine (F content: 62.2% by weight) is 86:13 (molar ratio of VDF/methyleneperfluorocyclopentane).

The said copolymer melts at 307° C. (DSC. melting enthalpy: 30 J/g). Polymer density: 2.19 g/cm$^3$.

Example 6

130 ml of deionised water was placed in a 0.3 l autoclave. 0.6 g of lithium perfluorooctyl sulphonate and 0.8 g of potassium peroxydisulphate were dissolved therein. This solution was adjusted by means of sodium hydroxide to a pH value of approximately 10. The closed autoclave was then subjected three times to a nitrogen pressure of 10 bar and each time subsequently released to normal pressure. 18 g of methyleneperfluorocyclopentane and 20 g of vinylidene fluoride were placed in the autoclave and the reaction mixture was heated to 70° C. with stirring. After a total reaction time of 10 h at 70° C., the mixture was cooled. After expiry of this period, during which the reaction pressure fell from 31 bar to 29 bar, the contents of the autoclave were cooled and the unreacted gas mixture was exhausted. The emulsion thus obtained was poured into 130 ml of a 4% aqueous solution of magnesium sulphate in order to achieve complete coagulation. The product was washed with water and dried, with 10 g of a copolymer (white powder) composed of units of vinylidene fluoride and methyleneperfluorocyclopentane being obtained.

The copolymer is likewise insoluble in the solvents named in Example 6.

The composition of the copolymer, determined by analysis of elemental fluorine (F content: 64.2% by weight) is 70:30 (molar ratio of VDF/methyleneperfluorocyclopentane).

The said copolymer melts at 308° C. (DSC. melting enthalpy: 23.6 J/g).

Example 7

In a manner similar to the procedure described in Example 6, 28 g of methyleneperfluorocyclopentane and 12 g of vinylidene fluoride were copolymerised. 5.1 g of a copolymer (white powder) composed of units of vinylidene fluoride and methyleneperfluorocyclopentane was obtained.

The copolymer is likewise insoluble in the solvents named in Example 5.

The composition of the copolymer, determined by analysis of elemental fluorine (F content: 63.8% by weight) is 73:27 (molar ratio of VDF/methyleneperfluorocyclopentane).

The said copolymer melts at 309° C. (DSC, melting enthalpy: 30.6 J/g).

Example 8

(Comparison example)

In a manner similar to the procedure described in Example 6, 34.2 g of hexafluoroisobutylene and 20 g of vinylidene fluoride were copolymerised. 9 g of a copolymer (white powder) composed of units of vinylidene fluoride and hexafluoroisobutylene was obtained.

The copolymer is likewise insoluble in the solvents named in Example 5.

The composition of the copolymer, determined by analysis of elemental fluorine (F content: 64.5% by weight) is 72:28 (molar ratio of VDF/HFiB).

The said copolymer melts at 303° C. (DSC, broadly expanded melting peak, melting enthalpy: 5.7 J/g).

An attempt was made to melt the polymers from the Examples 5, 7 and 8 in a melting crucible in air at 340° C. The following observations were made:

| Examples | Time | Observations |
| --- | --- | --- |
| 5 | 1 min | → colourless, melted, highly liquid |
|  | 25 min | → slight yellowing, highly liquid consistency of the melt is maintained |
| 7 | 0.5 min | → slight yellowing |
|  | 1 min | → melted, yellow |
| 8 | 0.5 min | → brown |
| (Comparison) | 1 min | → melted, highly viscous, deep brown |

Example 9

Copolymerisation of vinyl acetate in methyleneperfluorocyclopentane 100 g of 1,1,2,2,3,3-hexafluorocyclopentane was placed in a 300 ml glass flask and, after cooling to −50° C. 36.2 g of methyleneperfluorocyclopentane and 13.8 g of vinyl acetate as well as 0.3 g of diisopropyl peroxydicarbonate were added with stirring. The reaction apparatus was then evacuated 3 times to approximately 4 mbar and flushed each time with nitrogen. The reaction mixture was heated to 30° C. with constant stirring. The solids content of the solution was monitored during the reaction. It was 13.1% after 24 h and 24% after 45 h. After a total reaction time of 48 h at 30° C., the mixture was cooled. A colourless, viscous solution having a solids content of 25.2% by weight was obtained and precipitated by being stirred in ethanol. By this means 35 g of a white, pulverulent polymer was isolated.

The polymer is soluble in tetrahydrofuran and 1,1,2-trichlorotrifluoroethylene (R113) and insoluble in acetone, chloroform, dimethylformamide and dimethylacetamide. The Staudinger index [η] (also inherent viscosity) in THF is 0.1 dl/g.

The chemical composition was determined by $^1$H nuclear magnetic resonance spectroscopy (200 MHz in THF) (analysis of the signals at 5.7 ppm for CH and at 2 . . . 2.6 ppm for CH$_2$ and CH$_3$). According to this analysis the molar ratio of vinyl acetate to methyleneperfluorocyclopentane is 51:49 after 24 h polymerisation time and 47:53 after polymerisation has ended (48 h). In the IR spectrum an intensive band is observed at 1,679 cm$^{-1}$; this band is caused by the carbonyl vibration of the acetate radical.

A glass transition temperature at 92° C. (second heating) was established by DSC analysis. Melting ranges were not observed. A thermomechanical analysis was carried out against a press plate (4×4×1 mm). The material shows a typical thermoplastic softening which begins in the region of the glass transition temperature (90° to 100° C.) and ends at approx. 120° C.

Example 10

Saponification of vinyl acetate/methyleneperfluorocyclopentane polymers 5 g of the copolymer of vinyl acetate and methyleneperfluorocyclopentane prepared as in Example 9 was dissolved in 50 ml of tetrahydrofuran and added slowly with stirring to 33 ml of a suspension of THF and 2.25 g of potassium hydroxide (2.5 times the molar excess, referred to acetoxy groups). Following the exothermic reaction (temperature elevation from 22° to 24° C.), the solution was stirred for 3 h at 50° C. The polymer was then precipitated by being stirred in water which had been acidified to pH 1.8 by means of acetic acid, dried and reprecipitated twice from THF/H$_2$O. 2.8 g of a white to light beige powder was obtained. Solubility:

tetrahydrofuran (good)

1,1,2-trichlorotrifluoroethane (good)

acetone (partial)

1,1,1-trichloroethane (partial)

1,1,2,2,3,3-hexafluorocyclopentane (partial)

The Staudinger index in THF is 0.09 dl/g, from which it can be perceived that no decomposition has taken place, since the starting polymer (Example 9) exhibits an approximately identical [η] value of 0.1 dl/g (the small decrease can be attributed to the decrease in weight owing to the splitting off of acetate).

In the IR spectrum a decrease of 20% is observed in the relative intensity of the carbonyl vibration bands at 1,679 cm$^{-1}$ compared with the unsaponified starting polymer (Example 9). The terpolymer prepared according to this Example is therefore composed of 9 mol-% of vinyl alcohol units, 38 mol-% of vinyl acetate units and 53 mol-% of methyleneperfluorocyclopentane units.

This sample is also amorphous and exhibits a glass transition at 125° C. The partial hydrolysis therefore results in an elevation of the glass transition temperature.

We claim:

1. Methyleneperfluorocycloalkanes of the formula

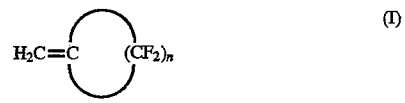

(I)

wherein n equals 3, 4 or 5.

2. 3,3,4,4,5,5,6,6-octafluoromethylenecyclopentane according to claim 1.

3. Method for the preparation of methyleneperfluorocycloalkanes of the formula (I) according to claim 1, having n equal to from 3 to 5, characterized in that ketene-producing compounds are reacted with perfluorocycloketones of the formula

(II)

at temperatures of from 340° to 1000° C., directly with one another or mixed with inert gases.

4. Polymer compositions, obtained by radical copolymerisation of
   a) from 10 to 52 mol-% of methyleneperfluorocycloalkanes according to claim 1, and
   b) from 90 to 48 mol % of vinylidene fluoride, vinyl fluoride, ethylene, vinyl acetate and/or vinyl alcohol (by saponification of vinyl ester copolymers).

5. A thermoplastic fluororesin comprising a polymer of a methyleneperfluoroalkane according to claim 1.

* * * * *